US012597492B2

(12) United States Patent
Zubarev et al.

(10) Patent No.: US 12,597,492 B2
(45) Date of Patent: Apr. 7, 2026

(54) TOPOLOGY-DRIVEN COMPLETION OF CHEMICAL DATA

(71) Applicant: International Business Machines Corporation, Armonk, NY (US)

(72) Inventors: Dmitry Zubarev, San Jose, CA (US); Petar Ristoski, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 697 days.

(21) Appl. No.: 17/101,912

(22) Filed: Nov. 23, 2020

(65) Prior Publication Data

US 2022/0165366 A1     May 26, 2022

(51) Int. Cl.
| | | |
|---|---|---|
| *G16C 20/50* | (2019.01) | |
| *G16C 20/30* | (2019.01) | |
| *G16C 20/70* | (2019.01) | |
| *G16C 20/80* | (2019.01) | |

(52) U.S. Cl.
CPC ............. *G16C 20/50* (2019.02); *G16C 20/30* (2019.02); *G16C 20/70* (2019.02); *G16C 20/80* (2019.02)

(58) Field of Classification Search
CPC ........ G16C 20/50; G16C 20/30; G16C 20/70; G16C 20/80; G16C 60/00; G16C 20/90
See application file for complete search history.

(56) References Cited

U.S. PATENT DOCUMENTS

| | | | |
|---|---|---|---|
| 6,219,622 B1 | 4/2001 | Schmidt | |
| 7,590,517 B2 | 9/2009 | Doerksen | |

| | | | |
|---|---|---|---|
| 2003/0134296 A1 | 7/2003 | Chen | |
| 2004/0088118 A1 | 5/2004 | Jensen | |
| 2017/0161635 A1 | 6/2017 | Oono et al. | |
| 2019/0304568 A1 | 10/2019 | Wei et al. | |
| 2019/0392304 A1 | 12/2019 | Aliper | |
| 2020/0090049 A1 | 3/2020 | Aliper | |
| 2020/0143910 A1 | 5/2020 | Noori | |

FOREIGN PATENT DOCUMENTS

| | | |
|---|---|---|
| CN | 110970099 A | 4/2020 |
| CN | 108416184 A | 6/2020 |
| CN | 111223532 A | 6/2020 |
| CN | 111370074 A | 7/2020 |
| CN | 116569266 A | 8/2023 |
| DE | 112021005313 T5 | 8/2023 |
| GB | 2616557 A | 9/2023 |

(Continued)

OTHER PUBLICATIONS

Lim, Jaechang, et al. "Scaffold-based molecular design with a graph generative model." Chemical science 11.4 (2020): 1153-1164. (Year: 2019).*

(Continued)

*Primary Examiner* — Karlheinz R. Skowronek
*Assistant Examiner* — Mary C Leverett
(74) *Attorney, Agent, or Firm* — Heather Schuler

(57)     ABSTRACT

A processor may receive molecular data for a plurality of molecules. The processor may perform topological data analysis on the molecular data to generate a molecular topological map. The processor may identify one or more lacunae in the molecular topological map. The processor may generate one or more additional molecules to fill at least one of the one or more lacunae.

20 Claims, 11 Drawing Sheets

(56)               References Cited

FOREIGN PATENT DOCUMENTS

| JP | 2021-068410 A | 4/2021 |
| JP | 2023-553784 A | 12/2023 |
| WO | 2019186196 A2 | 10/2019 |
| WO | 2022/105662 A1 | 5/2022 |

OTHER PUBLICATIONS

Pirashvili, Mariam, et al. "Improved understanding of aqueous solubility modeling through topological data analysis." Journal of cheminformatics 10.1 (2018): 1-14. (Year: 2018).*

Zubarev, Dmitry Yu, and Petar Ristoski. "Topology-Driven Generative Completion of Lacunae in Molecular Data." arXiv preprint arXiv:2208.00063 (2022). (Year: 2022).*

Samanta, Bidisha, et al. "NEVAE: A Deep Generative Model for Molecular Graphs." Journal of Machine Learning Research 21 (2020): 1-33. (Year: 2020).*

Li, Yibo, et al. "DeepScaffold: a comprehensive tool for scaffold-based de novo drug discovery using deep learning." Journal of chemical information and modeling 60.1 (2019): 77-91. (Year: 2019).*

Capecchi, Alice, Daniel Probst, and Jean-Louis Reymond. "One molecular fingerprint to rule them all: drugs, biomolecules, and the metabolome." Journal of cheminformatics 12 (2020): 1-15. (Year: 2020).*

Arús-Pous, J., et al., "SMILES-based deep generative scaffold decorator for de-novo drug design." Published in 2020. 18 pages. J Cheminform 12, 38. Published by BMC. https://doi.org/10.1186/s13321-020-00441-8.

Bjerrum, E., et al., "Improving Chemical Autoencoder Latent Space and Molecular De Novo Generation Diversity with Heteroencoders." Published Oct. 30, 2018. 17 pages. Published by MDPI. https://www.ncbi.nlm.nih.gov/pmc/articles/PMC6316879/.

Blaschke, T., et al., "Application of Generative Autoencoder in De Novo Molecular Design." Published Dec. 13, 2017. 11 pages. Molecular Informatics: vol. 37, Issue 1-2. Published by Wiley Online Library. https://doi.org/10.1002/minf.201700123.

Cravero, F., et al., "Computer-aided design of polymeric materials: Computational study for characterization of databases for prediction of mechanical properties under polydispersity." Published Jun. 19, 2019. 8 pages. Chemometrics and Intelligent Laboratory Systems 191 (2019) pp. 65-72. Published by Elsevier. https://doi.org/10.1016/j.chemolab.2019.06.006.

Dijkstra, E., "A Note on Two Problems in Connexion with Graphs." Published in 1959. 3 pages. Numerische Mathematik I, pp. 269-271.

Elton, D., et al., "Applying machine learning techniques to predict the properties of energetic materials." Published Jun. 13, 2018. 12 pages. Scientific Reports: vol. 8, Article No. 9059. Published by Scientific Reports. https://www.nature.com/articles/s41598-018-27344-x.

Gomez-Bombarelli, R., et al., "Automatic chemical design using a data-driven continuous representation of molecules." Published Jan. 12, 2018. 9 pages. ACS Cent. Sci. 2018, 4, 2, pp. 268-276. Published by ACS Publications. https://pubs.acs.org/doi/10.1021/acscentsci.7b00572.

Griffiths, R., et al., "Constrained Bayesian optimization for automatic chemical design using variational autoencoders." Published Nov. 18, 2019. 10 pages. Chem. Sci., 2020, 11, pp. 577-586. Published by The Royal Society of Chemistry. https://pubs.rsc.org/en/content/articlelanding/2020/sc/c9sc04026a#!divAbstract.

Hong, S., et al., "Molecular Generative Model Based on an Adversarially Regularized Autoencoder." Published Dec. 10, 2019. 8 pages. J. Chem. Inf. Model. 2020, 60, 29-36. Published by ACS Publications. https://pubs.acs.org/doi/10.1021/acs.jcim.9b00694.

Huan, T., et al., "A polymer dataset for accelerated property prediction and design." Published Mar. 1, 2016. 10 pages. Published by Scientific Reports. https://www.nature.com/articles/sdata201612.

Jin, W., et al., "Junction Tree Variational Autoencoder for Molecular Graph Generation." Published Mar. 29, 2019. 17 pages. Published by ARXIV. https://arxiv.org/abs/1802.04364.

Kuznetsova, N., et al., "Photoacid generators. Application and current state of development." Abstract Only. Accessed Nov. 23, 2020. 2 pages. Russian Chemical Reviews. vol. 89, No. 2. Published by IOP Science. http://dx.doi.org/10.1070/RCR4899.

Li, Y., et al., "Multi-Objective De Novo Drug Design with Conditional Graph Generative Model." Published Apr. 21, 2018. 22 pages. Published by ARXIV. https://arxiv.org/abs/1801.07299.

Li, Y., et al., "DeepScaffold: a comprehensive tool for scaffold-based de novo drug discovery using deep learning." Published Sep. 5, 2019. 39 pages. Published by ARXIV. https://arxiv.org/abs/1908.07209.

Lim, J., et al., "Scaffold-based molecular design with a graph generative model." Published Dec. 3, 2019. 12 pages. Chemical Science, 11, No. 4, pp. 1153-1164. Published by The Royal Society of Chemistry.

Lim, J., et al., "Molecular generative model based on conditional variational autoencoder for de novo molecular design." Published in 2018. 9 pages. Journal of Cheminformatics, 10(1), pp. 1-9, 2018. Published by Springer.

Liu, Q., et al., "Constrained Graph Variational Autoencoders for Molecule Design," Advances in Neural Information Processing Systems 31 (NIPS 2018), Montréal, Canada. http://papers.nips.cc/paper/8005-constrained-graph-variational-autoencoders-for-molecule.

Liu, Y., et al., "Materials discovery and design using machine learning." Published Aug. 8, 2017. 19 pages. Journal of Materiomics: vol. 3, Issue 3, pp. 159-177. Published by Science Direct. https://www.sciencedirect.com/science/article/pii/S2352847817300515.

Mannodi-Kanakkithodi, A., et al., "Machine Learning Strategy for Accelerated Design of Polymer Dielectrics." Published Feb. 15, 2016. 10 pages. Published by Scientific Reports. https://www.nature.com/articles/srep20952.

Mannodi-Kanakkithodi, A., et al., "Scoping the polymer genome: A roadmap for rational polymer dielectrics design and beyond." Published Sep. 2018. 12 pages. Materials Today: vol. 21, Issue 7, pp. 785-796. Published by Science Direct. https://www.sciencedirect.com/science/article/pii/S1369702117307344.

Mell, et al., "The NIST Definition of Cloud Computing," Recommendations of the National Institute of Standards and Technology, U.S. Department of Commerce, Special Publication 800-145, Sep. 2011, 7 pgs.

Moret, M., et al., "Generative molecular design in low data regimes." Published Mar. 2020. 10 pages. Nature Machine Intelligence, vol. 2, pp. 171-180. Published by Springer Nature. https://www.nature.com/articles/s42256-020-0160-y?proof=true.

Patra, T., et al., "Neural-Network-Biased Genetic Algorithms for Materials Design: Evolutionary Algorithms That Learn." Published Dec. 20, 2016. 12 pages. ACS Comb. Sci. 2017, 19, pp. 96-107. Published by ACS Publications. https://pubs.acs.org/doi/10.1021/acscombsci.6b00136.

Pilania, G., et al., "Accelerating materials property predictions using machine learning." Published Sep. 30, 2013. 6 pages. Published by Scientific Reports. https://www.ncbi.nlm.nih.gov/pmc/articles/PMC3786293/.

Prykhodko, O., et al., "A de novo molecular generation method using latent vector based generative adversarial network." Published Dec. 3, 2019. 13 pages. Published by BMC. https://www.ncbi.nlm.nih.gov/pmc/articles/PMC6892210/.

Singh, G., et al., "Topological Methods for the Analysis of High Dimensional Data Sets and 3D Object Recognition." Published in 2007. 11 pages. Eurographics Symposium on Point-Based Graphics. Published by The Eurographics Association.

Wang, C., et al., "Computational strategies for polymer dielectrics design." Published Jan. 14, 2014. 11 pages. Polymer: vol. 55, Issue 4, pp. 979-988. Published by Elsevier. https://www.sciencedirect.com/science/article/pii/S0032386113011889?via%3Dihub.

Wu, S., et al., "Machine-learning-assisted discovery of polymers with high thermal conductivity using a molecular design algorithm." Published Jun. 21, 2019. 11 pages. npj Computational

(56) References Cited

OTHER PUBLICATIONS

Materials vol. 5, Article No. 66. Published by Springer Nature. https://doi.org/10.1038/s41524-019-0203-2.

Xu, H., et al., "A Machine Learning-Based Design Representation Method for Designing Heterogeneous Microstructures." Published May 2015. 11 pages. Journal of Mechanical Design. Published by ResearchGate. https://www.researchgate.net/publication/272362195_A_Machine_Learning-Based_Design_Representation_Method_for_Designing_Heterogeneous_Microstructures.

Akaike, H., "Fitting Autoregressive Models for Prediction", Annals of the Institute of Statistical Mathematics, 21(1), Jun. 17, 1969, 5 pgs.

Carlsson, et al., "Fibres of Failure: Classifying Errors in Predictive Processes", arXiv:1803.00384v1 [cs.CV], Feb. 9, 2018, 10 pgs.

Crivello, J., "The Discovery and Development of Onium Salt Cationic Photoinitiators", Journal of Polymer Science Part A: Polymer Chemistry, 37(23):4241-4254, Aug. 15, 1999.

Devoe, et al., Photochemistry and Photophysics of Onium Salts, pp. 313-355. John Wiley & Sons, Ltd, Mar. 1993.

Edelsbrunner, et al., "Persistent Homology: Theory and Practice", European Congress of Mathematics, Krakow, Jul. 2-7, 2012, 20 pgs.

Elton, et al., "Deep learning for molecular design—a review of the state of the art", Molecular Systems Design & Engineering, 4, 828, May 22, 2019, DOI: 10.1039/c9me00039a, 22 pgs.

Goodfellow, et al., "Generative Adversarial Networks", arXiv preprint arXiv:1406.2661, Jun. 10, 2014, 9 pgs.

Guo, et al., "Identification of Key Features Using Topological Data Analysis for Accurate Prediction of Manufacturing System Outputs", Journal of Manufacturing Systems, 43, 10 pgs., Mar. 10, 2017, <http://dx.doi.org/10.1016/j.jmsy.2017.02.015>.

Hochreiter, et al., "Long short-term memory", Neural computation, 9(8):1735-1780, 1997.

Hofer, et al., "Photochemistry and initiation behavior of phenylethynyl onium salts as cationic photoinitiators", Journal of Polymer Science Part A: Polymer Chemistry, 47(13):3419-3430, May 27, 2009.

IBM Research, "Circa: Chemical information resources for cognitive analytics", Accessed on Jan. 15, 2021, <http://circa.res.ibm.com/>. 1 pgs.

International Search Report and Written Opinion, International Application No. PCT/CN2021/129960, International Filing Date Nov. 11, 2021.

Kingma, et al., "Auto-Encoding Variational Bayes", arXiv:1312.6114v11 [stat.ML], Dec. 10, 2022, 13 pgs.

Kozhushkov, et al., "Synthetic applications of sulfonium salts", European Journal of Inorganic Chemistry, 2020(26), Apr. 30, 2020, 15 pgs.

Krishnapriyan, et al., "Topological descriptors help predict guest adsorption in nanoporous materials", The Journal of Physical Chemistry C, 124(17):9360-9368, 2020, 14 pgs.

Kuznetsova, et al., "Photoacid Generators. Application and Current State of Development", Russian Chemical Reviews, 89(2), Jan. 2020, 19 pgs.

Landrum, G., Rdkit: Open-source cheminformatics. Downloaded from the Internet on Oct. 25, 2023, 2016, 2 pgs.

Langevin, et al., "Scaffold-constrained molecular generation", Journal of Chemical Information and Modeling, arXiv:2009.07778v3 [q-bio.QM], Oct. 5, 2020, 39 pgs.

Li, et al., "Multi-objective de novo drug design with conditional graph generative model", Journal of cheminformatics, 10(1), Jul. 24, 2018, 24 pgs. <https://doi.org/10.1186/s13321-018-0287-6>.

Lim, et al., "Scaffold-based molecular design with a graph generative model", Chem. Sci., 11, 153-1164, Dec. 3, 2019, DOI: 10.1039/c9sc04503a.

Nicolau, et al., "Topology Based Data Analysis Identifies a Subgroup of Breast Cancers With a Unique Mutational Profile and Excellent Survival", Proceedings of the National Academy of Sciences, 108(17):7265-7270, Feb. 25, 2011, 6 pgs.

Nielson, et al., "Topological Data Analysis for Discovery in Preclinical Spinal Cord Injury and Traumatic Brain Injury", Nature Communications, 6:8581, Oct. 14, 2015, DOI: 10.1038/ncomms9581, 12 pgs.

Offroy, et al., "Topological data analysis: A promising Big Data Exploration Tool in Biology, Analytical Chemistry and Physical Chemistry", Analytica Chimica Acta, 910, Mar. 3, 2016, 11 pgs.

Olivecrona, et al., "Molecular de-novo design through deep reinforcement learning", Journal of cheminformatics, 9(48):1-14, 2017, DOI 10.1186/s13321-017-0235-x.

Otter, et al., "A Roadmap for the Computation of Persistent Homology", EPJ Data Science, 6(17), 2017, DOI 10.1140/epjds/s13688-017-0109-5, 38 pgs.

Pan, et al., "Recent Progress on Generative Adversarial Networks (GANS): A survey", IEEE Access, 7:36322-36333, Apr. 2, 2019, Digital Object Identifier 10.1109/ACCESS.2019.2905015, 12 pgs.

Parida, et al., "Host Trait Prediction of Metagenomic Data for Topology-Based Visualization", In: Natarajan, R., Barua, G., Patra, M.R. (eds) Distributed Computing and Internet Technology. ICDCIT 2015. Lecture Notes in Computer Science, vol. 8956. Springer, Cham, 16 pgs., <https://doi.org/10.1007/978-3-319-14977-6_8>.

Pedregosa, et al., "Scikit-learn: Machine learning in Python", Journal of Machine Learning Research, 12, 2825-2830, Oct. 2011, 6 pgs.

Ristoski, et al., "Expert-in-the-Loop AI for Polymer Discovery", Proceedings of the 29th ACM International Conference on Information and Knowledge Management (CIKM'20), Oct. 19-23, 2020, Virtual Event, Ireland. ACM, New York, NY, USA, 8 pages, <https://doi.org/10.1145/3340531.3416020>.

Rizvi, et al., "Single-cell topological RNA-seq analysis reveals insights into cellular differentiation and development", Nature Biotechnology, 35, May 1, 2017, 14 pgs., doi:10.1038/nbt.3854.

Rumelhart, et al., "Learning representations by back-propagating errors", Nature, vol. 323, Oct. 9, 1986, 4 pgs.

Sanchez-Lengeling, et al., "Inverse Molecular Design Using Machine Learning: Generative Models for Matter Engineering", Science, 361(6400), Jul. 27, 2018, 7 pgs.

Schwalbe_Koda, et al., "Generative models for automatic chemical design", Machine Learning Meets Quantum Physics, Lecture Notes in Physics 968, Jun. 4, 2020, 23 pgs., <https://doi.org/10.1007/978-3-030-40245-7_21>.

Singh, et al., "Topological methods for the analysis of high dimensional data sets and 3d object recognition", Eurographics Symposium on Point-Based Graphics, Jan. 2007, 11 pgs., DOI:10.2312/SPBG/SPBG07/091-100.

Tauzin, et al., "giotto-tda: A Topological Data Analysis Toolkit for Machine Learning and Data Exploration", Journal of Machine Learning Research, 22(39):1-6, Jan. 2021.

Tsarevsky, et al., "The Onium Compounds", Journal of Chemical Education, vol. 74, No. Jun. 6, 1997, 3 pgs.

Wasserman, L., "Topological Data Analysis. Annual Review of Statistics and Its Application", 5(1), 2018, First published on Dec. 13, 2017, 34 pgs., <https://doi.org/10.1146/annurev-statistics-031017-100045>.

Zubarev, et al., "Cognitive Materials Discovery and Onset of the 5th Discovery Paradigm", Chapter 6, pp. 103-120. Oxford University Press, Nov. 20, 2019.

Japan Patent Office, "Notice of Reasons for Refusal" May 22, 2025, 09 Pages, JP Application No. 2023-524956.

Pirashvili et al., "Improved understanding of aqueous solubility modeling through topological data analysis", Journal of Cheminformatics, Nov. 2018, 14 pages, doi: https://doi.org/10.1186/s13321-018-0308-5.

The State Intellectual Property Office of People's Republic of China, "First Office Action", Jul. 16, 2025, 18 Pages, CN Application No. 202180078086.8.

The State Intellectual Property Office of People's Republic of China, "Second Office Action", Dec. 5, 2025, 17 Pages, CN Application No. 202180078086.8.

Zubarev D et al., "Topology-Driven Completion of Chemical Data", 2020 MRS Virtual Spring/Fall Meeting, Nov. 27-Dec. 4, 2020, 1915 pages.

* cited by examiner

400

420

422

424

426

410

412

414

416

TOPOLOGY-DRIVEN COMPLETION OF CHEMICAL DATA

BACKGROUND

The present disclosure relates generally to the field of materials science, and more specifically to polymer design, discovery, and synthesis.

Molecular discovery, design, synthesis, and testing often takes a substantial amount of time. The process may be accelerated through various computational tools. Such tools may produce an overwhelming number of generated molecular candidates, and the generated molecular candidates frequently fail to have desired attributes. The result is deficiencies in adequately exploring families of materials with desired attributes and a lot of time, money, and energy misspent testing candidates that are infeasible or feasible but do not meet target requirements.

SUMMARY

Embodiments of the present disclosure include a system, method, and computer program product for generating new molecules.

In some embodiments, a processor may receive molecular data for a plurality of molecules. The processor may perform topological data analysis on the molecular data to generate a molecular topological map. The processor may identify one or more lacunae in the molecular topological map. The processor may generate one or more additional molecules to fill at least one of the lacunae.

In some embodiments of the present disclosure, the plurality of molecules have one or more molecular properties in common.

In some embodiments of the present disclosure, a molecular scaffold may be generated for each of the plurality of molecules. In some embodiments, a generative potential score may be generated for each scaffold.

In some embodiments of the present disclosure, the plurality of molecules may share a molecular scaffold, and the one or more additional molecules may contain the molecular scaffold In some embodiments of the present disclosure, the one or more additional molecules are generated using a variational autoencoder. In some embodiments, the variational autoencoder may be conditioned via scaffold-conditioning such that the one or more additional molecules contain a specified molecular scaffold. In some embodiments, the variational autoencoder has a variational autoencoder loss function, and the variational autoencoder loss function is modified to include a generative potential of the specified molecular scaffold.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
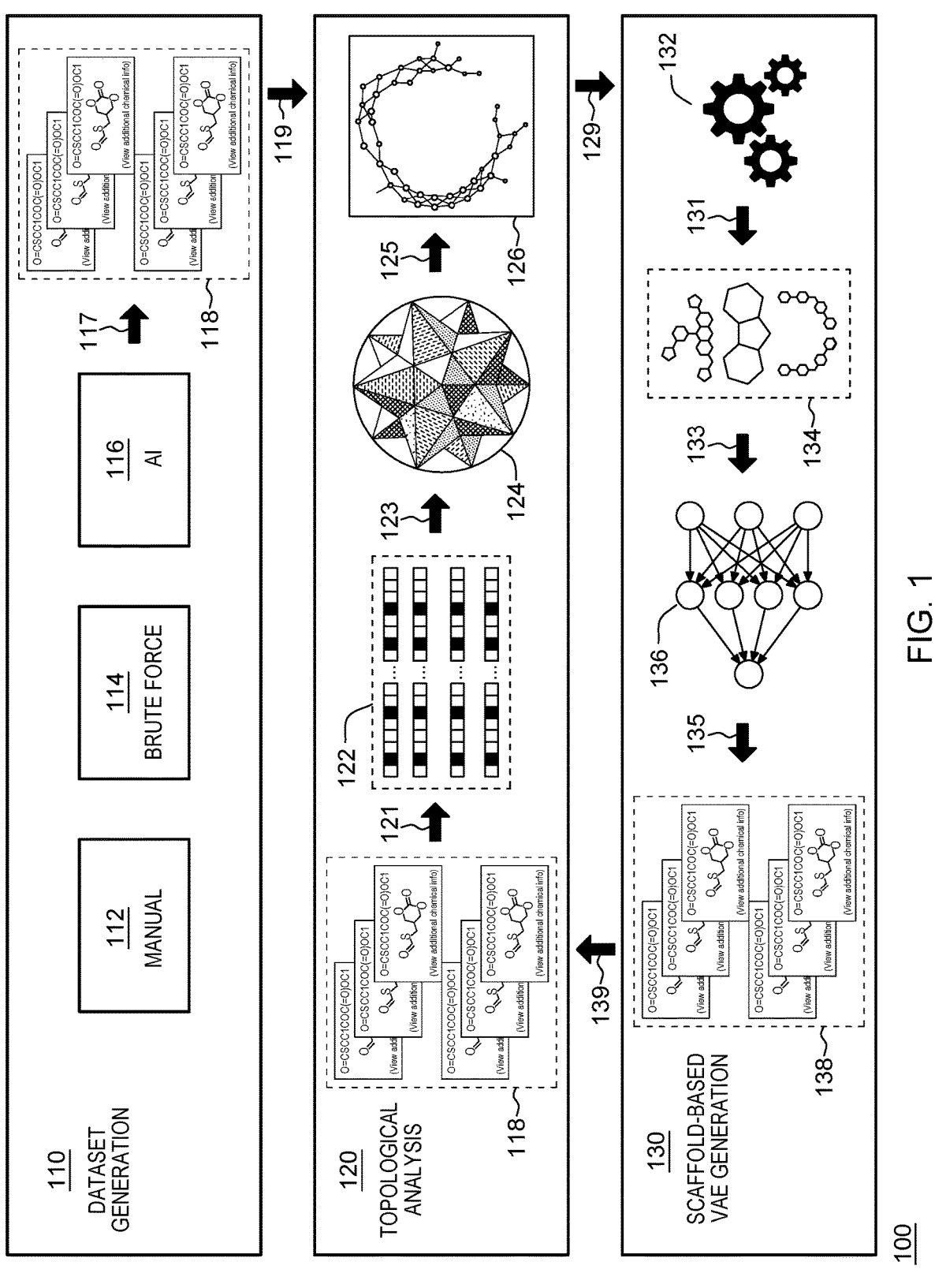
FIG. 1 illustrates a pipeline of new molecule generation according to embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate generally to the field of materials science, and more specifically to polymer synthesis. It will be readily understood that the instant components, as generally described and illustrated in the figures herein, may be arranged and designed in a wide variety of different configurations. Thus, the following detailed description of the embodiments of at least one of a method, apparatus, non-transitory computer readable medium, and system, as represented in the attached figures, is not intended to limit the scope of the application as claimed but is merely representative of selected embodiments.

The instant features, structures, or characteristics as described throughout this specification may be combined or removed in any suitable manner in one or more embodiments. For example, the usage of the phrases "example embodiments," "some embodiments," or other similar language throughout this specification refers to the fact that a particular feature, structure, or characteristic described in connection with the embodiment may be included in at least one embodiment. Thus, appearances of the phrases "example embodiments," "in some embodiments," "in other embodiments," or other similar language throughout this specification do not necessarily all refer to the same group of embodiments, and the described features, structures, or characteristics may be combined or removed in any suitable manner in one or more embodiments. Further, in the diagrams, any connection between elements can permit one-way and/or two-way communication even if the depicted connection is a one-way or a two-way arrow. Also, any device depicted in the drawings can be a different device. For example, if a mobile device is shown sending information, a wired device can also be used to send the information.

Molecular discovery often takes a substantial amount of time. For example, introducing a new polymer material to the market may require over ten years of design, synthesis, and testing. The process may be accelerated through computational design of molecules using tools such as combinatorial screening, inverse design, generative modeling, and reinforcement learning. Such tools may produce many computer-generated candidates, often on the scale of 10,000, 000s of candidates. However, molecular candidates achieved via these tools frequently fail to have desired attributes such as synthetic viability, robust polymerization, and compliance with internal and external regulations. The result is a lot of time, money, and energy misspent testing candidates that do not meet requirements.

Historical data driving the computational design and generation of new molecular candidates is incomplete and predisposed. Such deficiencies may lead to the amplification of molecular candidates which lack novelty, lack necessary attributes, and have other undesirable characteristics. Moreover, these deficiencies may result in failure to identify unexplored families of materials, reduce discovery efficiency, and increase unnecessary costs of testing and experimental follow-through.

Experimental follow-through is critical in the development of new molecules whether in the materials domain, food science, conservation science, pharmacology, or any other field that benefits from the generation of new molecules. Data acquisition strategies bridging computational and experimental stages of molecular discovery are able to elucidate missing pieces of historical data, complete missing segments using guided candidate generation, and enrich the experimental phase with a greater percentage of successful outcomes.

The present disclosure enables such data acquisition by filling in missing parts of initial datasets to complete the datasets with molecules previously overlooked. Topological data analysis based on a graph (such as a Reeb graph) may reveal lacunae in the available data hinder efficient molecular discovery; the present disclosure may use the lacunae to complete the data.

The present disclosure may use known molecular information as a launch point to find viable molecular candidates. The present disclosure may be described as the exploration of an unknown area on a map to discover terrain details and fill the map in with the newly discovered details: it uses what is known (e.g., the edge of the known world) to launch the exploration into what is known to be unknown so as to fill in the details about the unknown. The present disclosure may be likened to a gardener patching a hole in the garden: it starts on firm footing to patch the edge of the hole and works its way in until the hole is fully patched. The present disclosure may be likened to repairing clothing with a patch: the patch is attached to material known to be solid, extends over a hole, and attaches on the other side to more material known to be solid. The present disclosure may use the known molecular data on the border of the known to discover new data.

Those skilled in the art will recognize that the present disclosure is applicable for generating candidates for any chemical dataset. For example, pharmaceutical, polymer materials, and other fields which may benefit from the generation of unknown organic or inorganic molecules may benefit from the present disclosure. Polymer materials includes, for example, generation of ring-opening polymerization of cyclic lactones (including monomers and catalysts), polyimide block copolymers, and polyacrylates. For brevity and clarity, the present disclosure focuses the discussion on components of photoresists such as photoacid generator (PAG) molecules. PAG molecules are frequently used for chemically amplified lithography, medicine, microfluidics, and three-dimensional (3D) printing.

The present disclosure may impose constraints informed by the topological features of the data on a generative procedure to avoid trivial or undesirable molecular candidates, thereby reducing experimental costs by focusing on molecules most likely to meet various requirements. Topological features may be illustrated by a topological data analysis graph. For example, loops and flares on a Reeb graph may indicate existence of unknown molecular candidates worth pursuing. The present disclosure is compatible with other approaches of new molecule generation and facilitation of highly actionable or otherwise highly desirable candidates. For example, including an expert in the loop by exposing a subject matter expert (SME) to the data and enabling the SME to evaluate the data to determine which datasets are most likely to produce desirable results.

The present disclosure may actively use attributes assigned to molecules. The attributes may be diverse: position in the dataset, physical properties, National Fire Protection Association (NFPA) hazard identification or other labels, and other attributes. These attributes may be used to construct a Reeb graph. In a Reeb graph, attributes (including scalar attributes) may be used as a filter function for an initial data projection.

The present disclosure may use known molecules with similar attributes to generate molecular candidates with the same or similar attributes. The present disclosure may be likened to kitchen artists developing new recipes: a chocolate chip cookie recipe may be combined with recipes of other desserts (e.g., peanut butter cookies, cakes, and brownies) to achieve a sweet treat whereas it is less likely to be combined with recipes of a main course (e.g., steak, tofu, seitan, or macaroni) if the goal is to design a new dessert (e.g., the "scaffold" of a dessert group may be sugar, flour, and salt and the "functional groups" of the resulting dessert options may be flavoring such as vanilla, chocolate, and/or cinnamon). In some embodiments, by limiting the discovery process to specified scaffolds (e.g., scaffolds known to have desired attributes), the search results can be limited to the most viable and desirable molecular candidates.

Limiting molecular candidates to a condition-specific approach (e.g., by requiring candidates to have a certain scaffold) may significantly decrease non-viable candidates, thereby significantly decreasing review costs. In a comparison between previous approaches and the approach of the present disclosure, a previous approach generated 44,000 molecular candidates whereas the approach of the present disclosure generated 137 molecular candidates, drastically increasing the efficiency of the experimental phase. In this example, the 44,000 candidates generated by the establishment approach failed to change the topology of the data in any meaningful way whereas the 137 molecular candidates discovered by means of the present disclosure changed the topology of the data by adding missing data to the dataset using internal diagnostics of failure and success to elucidate the most viable molecular candidates.

In the present disclosure, the input dataset reflects upon the output data because the present disclosure uses a data-driven approach. The present disclosure may use one dataset to make one graph for one set of results, multiple datasets for multiple graphs for multiple sets of (potentially related) results, combine multiple datasets into one graph for one set of results (e.g., seeking molecular candidates with hybrid qualities), or some combination thereof.

An initial dataset may include a set of molecules such as a set of iconic PAGs from the sulfonium and iodonium families. New molecules may be PAG-like candidates likely to demonstrate desired photo-chemical behavior, a currently inaccessible level of environmental benignity, and other pursued attributes. The present disclosure acts as a control module in that it improves the signal-to-noise ratio.

FIG. 1 illustrates a pipeline of molecule generation 100 according to embodiments of the present disclosure. In some embodiments of the present disclosure, three main operations: dataset generation 110, topological analysis 120, and scaffold-based VAE generation 130 are employed to develop new molecules. A dataset 118 from dataset generation 110 may be submitted for topological analysis 120. The topological analysis result 126 may then be used for scaffold-based VAE molecule generation 130.

Dataset generation 110 may occur in a variety of ways. A dataset 118 may be compiled 117 manually 112, using brute force 114, and/or using artificial intelligence (AI) 116. The dataset 118 may be submitted 119 for topological analysis 120.

Topological analysis 120 may involve taking a dataset 118 and applying a kernel 121 to generate molecular fingerprints 122. Molecular fingerprints 122 may be submitted for topological data analysis 124 to produce 125 topological analysis results 126. The topological analysis results 126 may be a compilation of data such as a topological graph or a Reeb graph.

Topological analysis results 126 may be submitted 129 for scaffold analysis 132 of the scaffold-based generation 130 operation. Scaffold analysis 132 may generate 131 scaffolds 134 for molecules within the molecular dataset 118. Scaffolds 134 may be submitted 133 to an encoder 136. An encoder 136 may be scaffold-conditioned, such as a scaffold-conditioned variational auto-encoder (VAE). The encoder 136 produces 135 new molecules 138. New molecules 139 may be submitted for topological analysis 120 for further study and the addition of further new molecules.

Figure 2A:
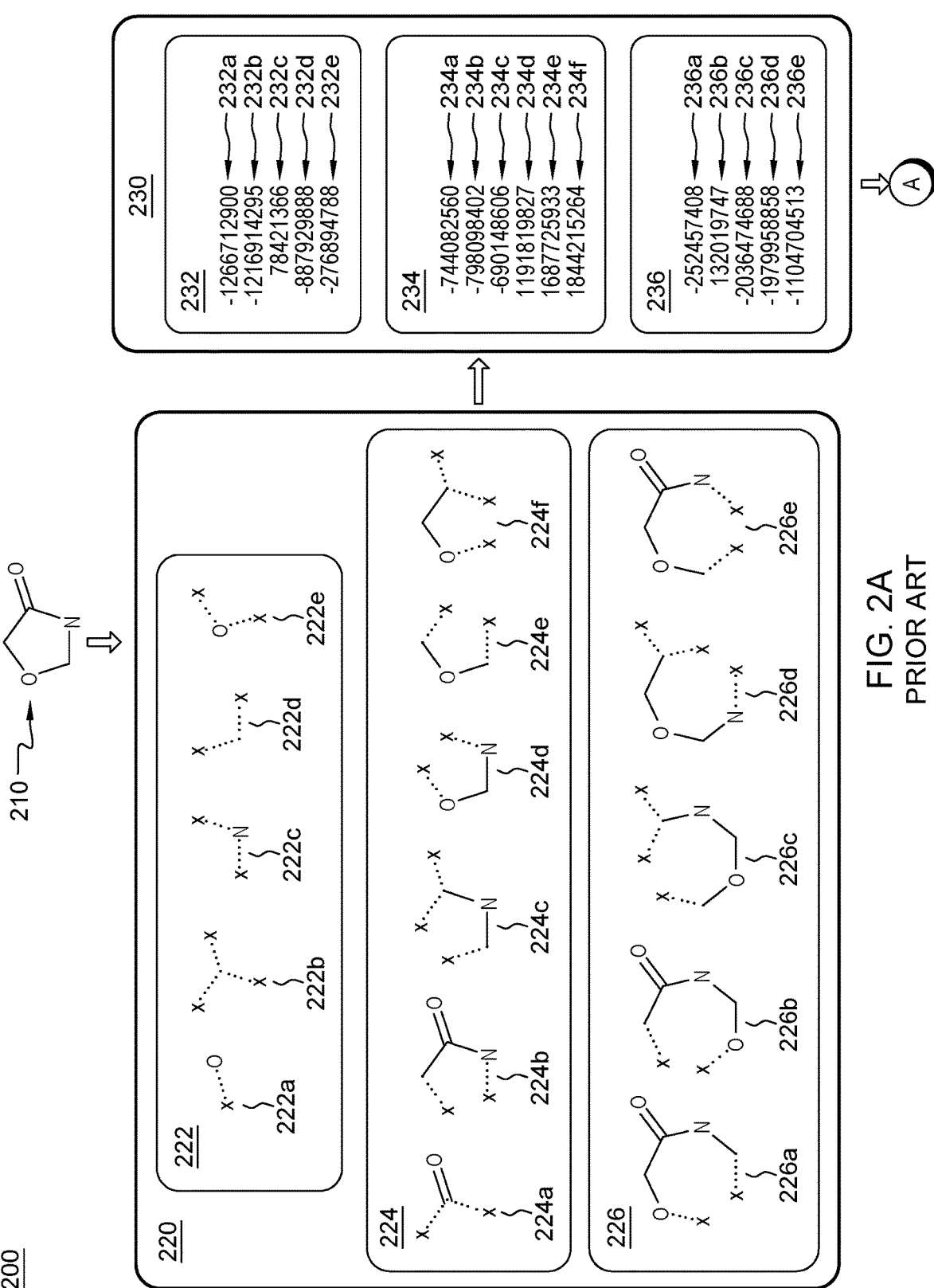
FIG. 2A illustrates generating identifiers in accordance with embodiments of the present disclosure.
Figure 2B:
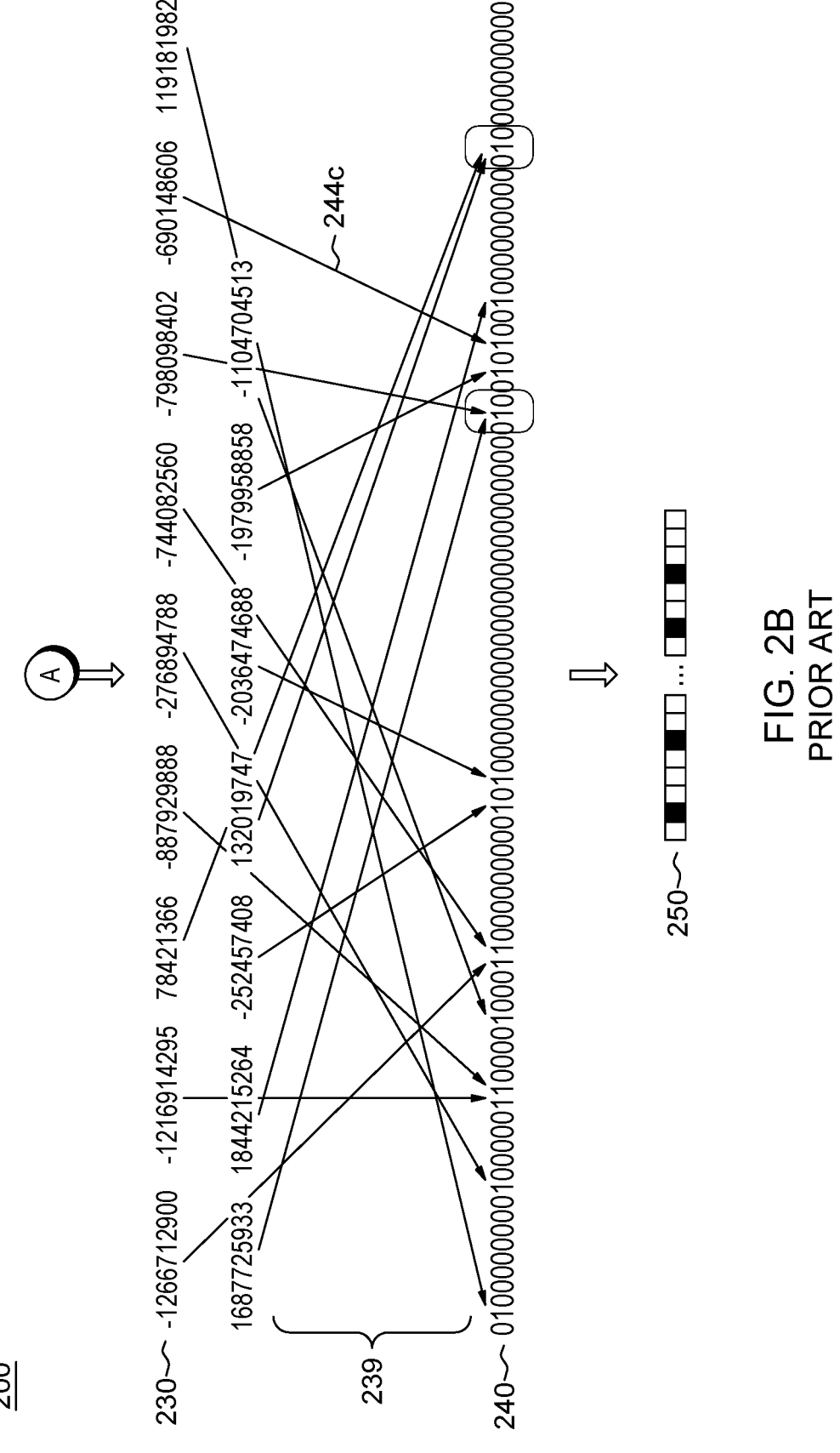
FIG. 2B illustrates using identifiers to generate bit vectors in accordance with embodiments of the present disclosure.

A molecular dataset 118 may be submitted 119 for topological analysis 120, as will be further explained in the discussions of FIGS. 2A and 2B.

FIG. 2A illustrates generating identifiers 230 from molecules 210 in accordance with embodiments of the present disclosure, and FIG. 2B illustrates generating fingerprints 250 from identifiers 230 in accordance with embodiments of the present disclosure. FIG. 2A and FIG. 2B may be considered an illustration of an operation 121 of FIG. 1.

FIG. 2A illustrates generating identifiers 230 from a molecule 210. Molecules 210 may be derived into derivations 220 which may be used to generate identifiers 230 which may be used to generate binary representation 240 and, ultimately, a molecular fingerprint 250 (FIG. 2B). Those skilled in the art will recognize that any method for generating identifiers 230 and molecular fingerprints 250 may be used in accordance with the present disclosure.

Molecular derivations 220 may be derived from a molecule 210. Molecules 210 may be derived into a variety of diameters. The diameter of a fragment refers to the number of bonds from the center of the fragment. A zero diameter fragment refers to a fragment with zero bonds; in other words, a fragment with a diameter of zero describes only the center atom of the fragment. Larger fragments build outward from a zero diameter fragment. A fragment with a diameter of two includes the center atom of the fragment and the atoms bonded directly to it; a fragment with a diameter of four includes the center atom of the fragment, the atoms bonded directly to the center atom, and any atoms bonded to the atoms bonded directly to the center atom.

Diameter zero derivations 222a, 222b, 222c, 222d, and 222e are shown in the first derivations block 222. Diameter two derivations 224a, 224b, 224c, 224d, 222e, and 222f are shown in the second derivations block 224. Diameter four derivations 226a, 226b, 226c, 226d, and 226e are shown in the third derivations block 226. It may be advantageous to generate molecular derivations 220 of various diameters 222, 224, and 226.

Molecular derivations 220 may be used to generate identifiers 230. Identifiers of diameter zero derivations 232a, 232b, 232c, 232d, and 232e are shown in the first identifiers block 232. Identifiers of diameter two derivations 234a, 234b, 234c, 234d, 232e, and 232f are shown in the second identifiers block 234. Identifiers of diameter four derivations 236a, 236b, 236c, 236d, and 236e are shown in the third identifiers block 236.

FIG. 2B illustrates using identifiers 230 to generate bit vectors 240 what may be used to generate a molecular fingerprint 250. Identifiers 230 are hashed 239 to produce a fixed-length binary representation 240. An individual identifier 234c is hashed 244c to produce a part of the fixed-length binary representation 240. The fixed-length binary representation 240 is then used to generate a molecular fingerprint 250. A molecular fingerprint 250 may also be referred to as a bit vector fingerprint 250.

A molecular fingerprint 250 illustrates the presence or absence of structural motifs. A kernel may extract features of a molecule, hash 239 the molecular features, and use the hash (e.g., the binary representation 240) to determine the bits of the molecular fingerprint 250. In some embodiments, fingerprints, molecular fingerprints 250 range in size from 1,000-4,000 bits. A molecular fingerprint 250 may be used to generate 123 a topological data analysis graph 124 as shown in FIG. 1.

Figure 3:
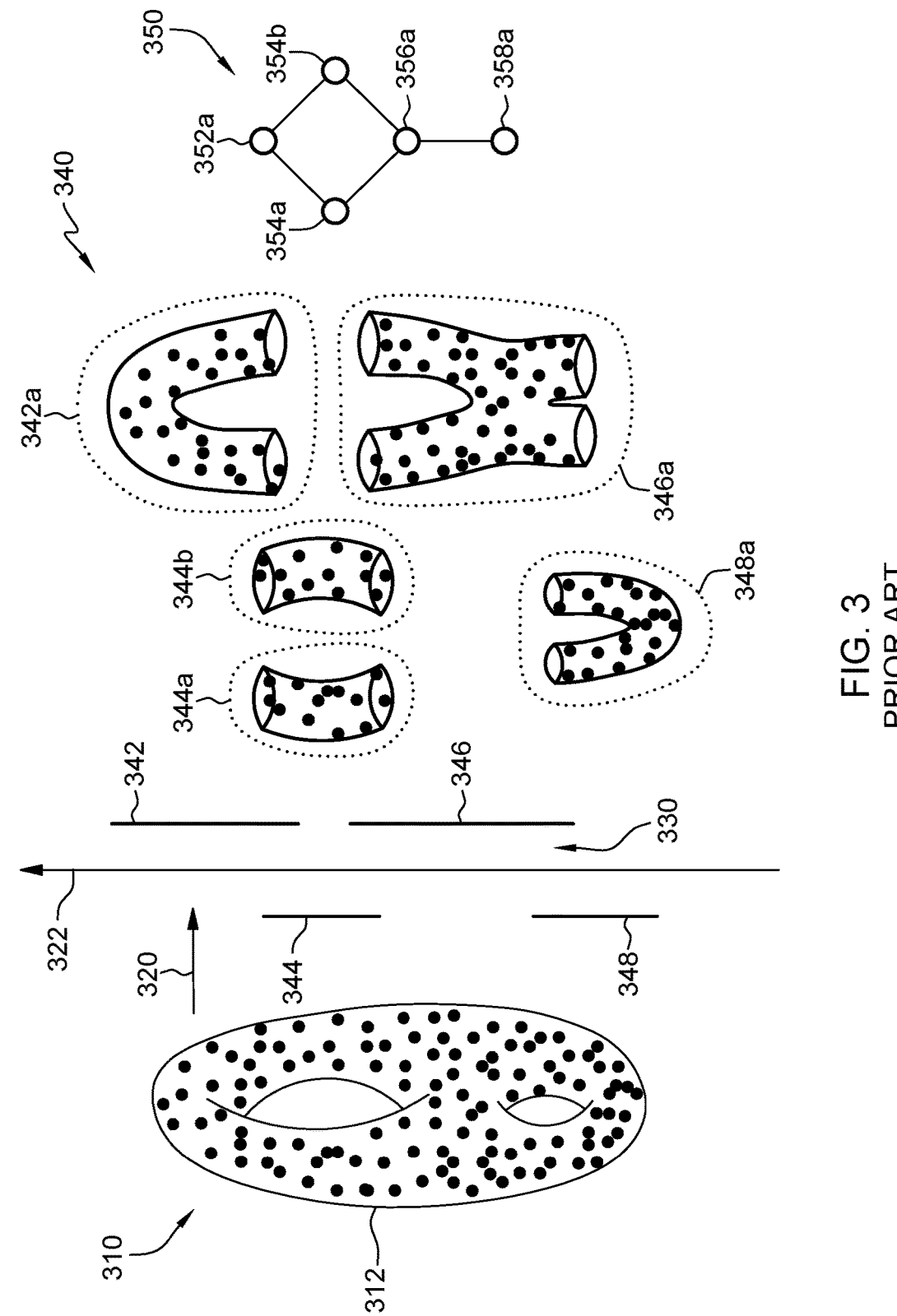
FIG. 3 illustrates topological data analysis in accordance with embodiments of the present disclosure.

FIG. 3 illustrates topological data analysis 300 in accordance with embodiments of the present disclosure. FIG. 3 may be considered an illustration of using a topological data analysis graph 124 to generate 125 a topological graph 126 as shown in FIG. 1.

A Reeb graph, or an approximation thereof such as an adjacent graph 350, may be obtained from a three-dimensional or higher dimensional model such as a point cloud 312. An algorithm may be used on a topological data analysis. The algorithm may be a Mapper algorithm or any other method used for the construction of a Reeb graph and/or Reeb graph approximation. The algorithm may combine the construction of a Reeb graph approximation with a pull-back cover on the data.

Each molecule in the dataset may be represented by a bit vector and generated as a molecular topological fingerprint. For example, a PAG may be represented by a Morgan fingerprint (MorganFP). A molecular dataset may be treated as a point cloud 312 with pair-wise distances. Pair-wise distances may be defined using any available chemoinformatic approach. The various dots in the matrix construction point cloud 312 each represent a molecular fingerprint. The molecular dataset may be treated as a point cloud 312 in the space of bit vectors 310.

Dice similarity may be used on bit vectors to define pairwise distances on the set of molecules. Distance to the reference point may be used as a filter function in topological data analysis. For example, a reference point may be the PAG with the smallest number of heavy atoms in the dataset, and the distance to that PAG may be used in filtering data in the topological data analysis graph. The filter function $f$ 320 may split the landscape of the point cloud 312 with respect to the height of the point cloud 312. Alternative arrangements for splitting the point cloud 312 are suitable for use in accordance with the present disclosure such as, for example, splitting the point cloud vertically or otherwise reorienting the point cloud 312 prior to splitting.

Overlapping range splitters 342, 344, 346, and 348 may be used to split the point cloud 312 into various overlapping segments 342a, 344a, 344b, 346a, and 348a. Molecules may be assigned to segment sets 340 based on values of the filter function ƒ 320. Segments 342a, 344a, 344b, 346a, and 348a may also be referred to as levels 342a, 344a, 344b, 346a, and 348a, and a segment set 340 may also be referred to as a level set 340.

An algorithm may be used to produce a simplified description of the data in the form of a graph. The algorithm may be a computational method for extracting simple descriptions of high dimensional data sets in the form of simplicial complexes (e.g., Mapper). The graph may be described with the equation G=(C, E) wherein G is the graph, C is a set of clusters represented as nodes, and E is the set of all edges. Each node in the graph represents a cluster C of molecules and an edge E between clusters indicates overlap between the clusters. Other rules of establishing connection between nodes may used depending on the choice of approximation of Reeb graph.

An algorithmically generated graph (e.g., a Mapper graph) may directly visualize various aspects of data shapes. For example, loops (which may also be referred to as holes) and flares (which may also be referred to as branches) may be visible in the graphical shape of the data. Loops and/or flares in the data indicate missing data, pinpointing where to look for new molecules as new molecules that fill loops and close flares are likely to be desirable molecules.

Segment sets 340 may be clustered into disjointed sets using agglomerative clustering on precomputed dice distances to identify connected and disconnected components. A cluster 342a, 344a, 344b, 346a, and 348a may be represented as a node 352a, 354a, 354b, 356a, and 358a on a graph 350 such as a Mapper graph 350. Nodes 352a, 354a, 354b, 356a, and 358a may be connected to each other via links if the connected nodes have common members.

For example, the first segment cluster 342a has common members with both members of second segment cluster 344a and 344b because of the overlapping range splitter 342 used to split the sever the first segment cluster 342a from the second segment clusters 344a and 344b; thus, as the clusters share molecular fingerprints, links connect the first segment node 352a to each of the second segment nodes 354a and 354b. Note that the second segment nodes 354a and 354b are not linked because the second segment clusters 344a and 344b do not share common molecular fingerprints because there is no overlap between the two second segment clusters 344a and 344b.

Mapping a molecular database in this way rigorously captures aspects of the shape of the dataset such as loops and flares. Flares may also be referred to as branches. Loops and flares show lacunae; lacunae indicate gaps or holes in the data which are ripe for molecular generation. A graph such as a Mapper graph 350 may be submitted 129 for scaffold-based generation of new molecules 130 as shown in FIG. 1.

Figure 4:
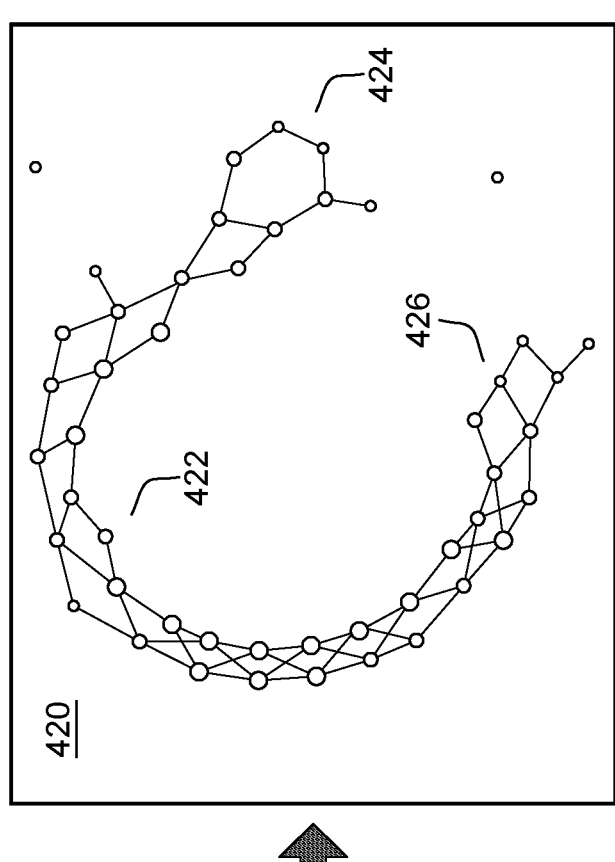
FIG. 4 illustrates generating molecular candidates in accordance with embodiments of the present disclosure.
Figure 4:
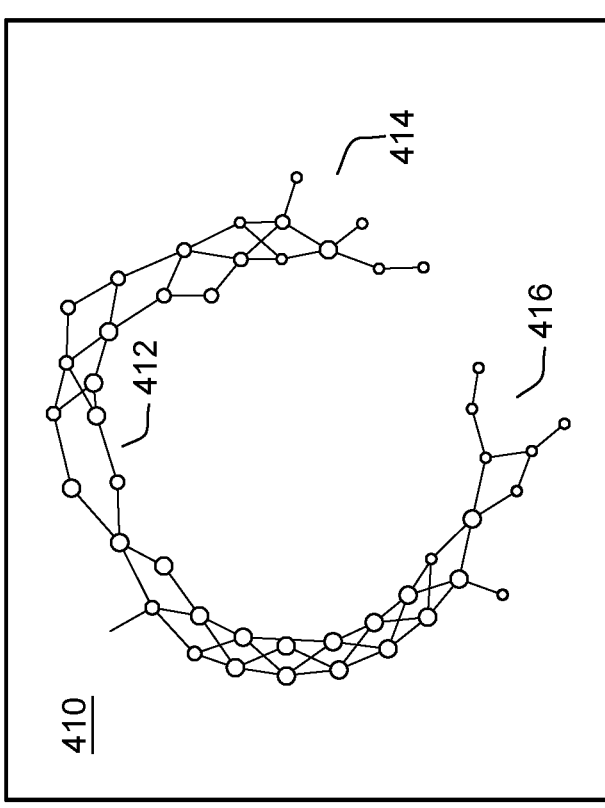

FIG. 4 illustrates generation molecular candidates 400 in accordance with embodiments of the present disclosure. A topological data analysis graph 410 may be submitted for scaffold-based generation to produce a more complete topological graph 420.

Topological data analysis graph 410 may have loops 412 and flares 414 and 416. Loops 412 and flares 414 and 416 may indicate that new molecules may be derived from the dataset. A loop 412 in a topological graph 410 may be described as a space that will permit one or more additional unique links between nodes. A flare 414 and 416 in a topological graph 410 may be described as a node with only one link, a loose edge, or space in a topological graph 410 where a molecular point appears to be dangling.

Submitting an input topological data analysis graph 410 to scaffold-based molecular generation 130 (FIG. 1) may result in an output topological data analysis graph 420. By undergoing scaffold-based molecular generation 130, additional molecules were added. Specifically, by the addition of scaffold-based molecular generation molecules, loop 412 was tightened to a smaller loop 422 and flares 414 and 416 were closed into loops 424 and 426. Output topological data analysis graph 420 can be submitted for further scaffold-based molecular generation 130 (shown in FIG. 1) as it may further tighten loops 424 and 426 and close flares.

The addition of nodes on topological data analysis graphs 410 and 420 represents the addition of molecules to the dataset. In other words, added nodes mean new molecules. New molecules derived or discovered using the present disclosure improve completion of a chemical dataset and are relatively likely to be worth pursuing with respect to seeking molecules with highly desirable attributes.

Figure 5:
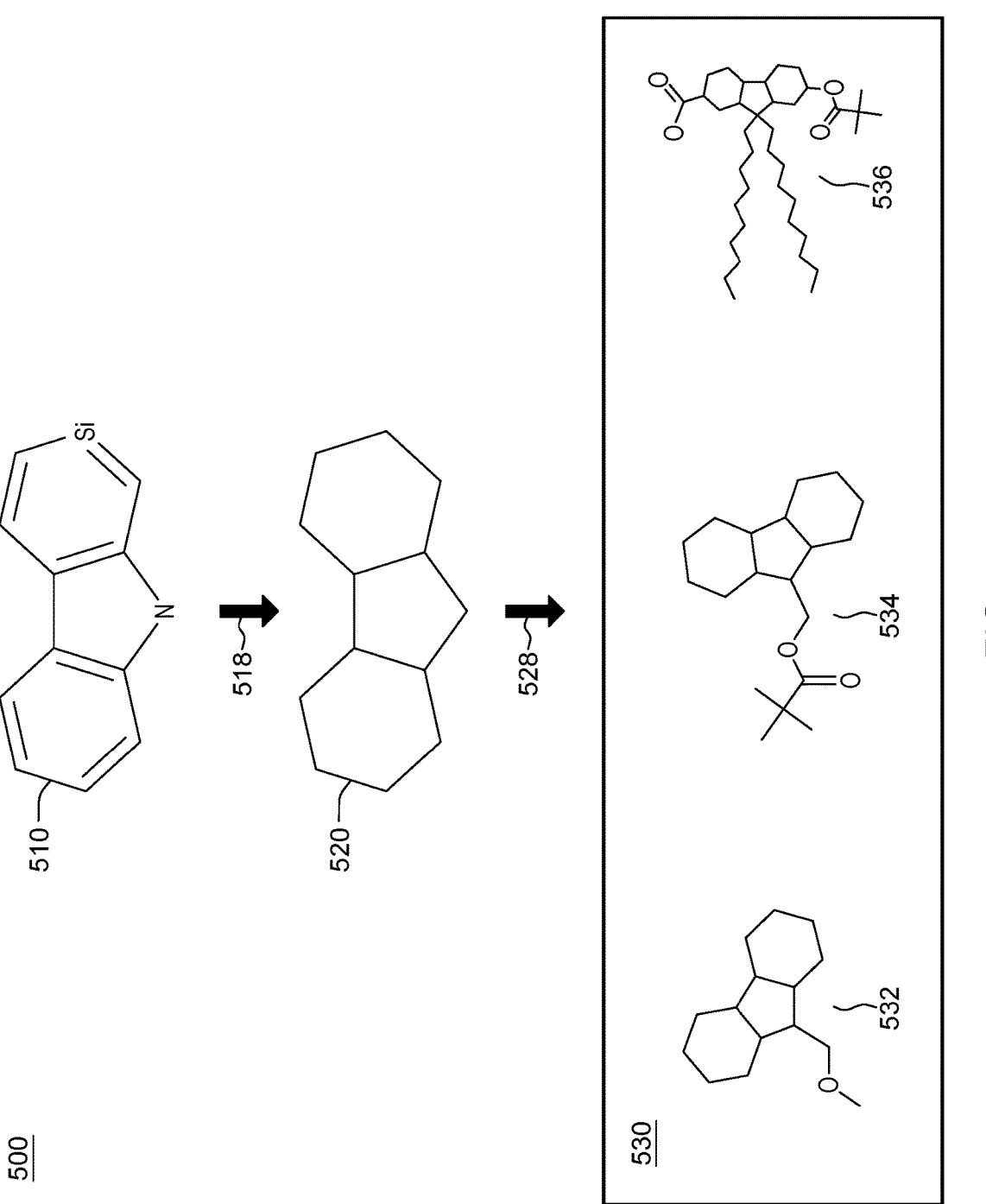
FIG. 5 illustrates scaffold analysis molecule generation in accordance with embodiments of the present disclosure.

FIG. 5 illustrates scaffold analysis molecule generation 500 in accordance with embodiments of the present disclosure. A molecular scaffold may represent the core of a molecule; the core of a molecule may be described as the molecule without functional groups. A scaffold may be considered the primary constraint on the shape of the molecule. A scaffold may be considered the primary constraint on the basic properties of the molecule.

Scaffolds enable hierarchical representation of molecules. Scaffold hierarchies can be built to offer different levels of abstraction in the representation of a molecule. Analysis of scaffolds uses definitions and existing hierarchies and their implementations. An example of an informational database which may be useful for scaffold analysis is a cheminformatic toolkit.

In a scaffold analysis molecule generation process 500 as shown in FIG. 5, functional groups are removed 518 from a molecule 510 to obtain the scaffold 520 of the molecule 510. The scaffold 520 may then be used as a basis for generating 528 an assortment 530 of generated molecules 532, 534, and 536.

Generated molecules 532, 534, and 536 may have similar, different, more, or fewer functional groups than the molecule 510 from which the scaffold 520 was generated. A commonality between generated molecules 532, 534, and 536 is the scaffold 520 used to generate 528 the molecules 532, 534, and 536. Molecules generated from a scaffold may have different functional groups added to the same atom. For example, two molecules 532 and 534 have distinct functional groups added to the scaffold at the same point. Molecules generated from a scaffold may have the same or different functional groups added to one or more different atoms. For example, the first of the generated molecules 532 and the third of the generated molecules 536 have functional groups added to different atoms of each molecule 532 and 536. Functional groups may be bonded to any atom in the scaffold which will support the bond.

For scaffold analysis, an undirected graph may be written as G=(C, E). All of the scaffolds in a dataset S={s₁, s₂, . . . , sₙ} may be identified. Each scaffold s in the dataset may appear in one or more clusters $C_S=\{c_1, c_2, \ldots c_S\}$ and the scaffold s may be identified in each of the clusters Cs the scaffold s is in. As clusters may be analyzed to become nodes, either clusters or nodes may be used for the analysis. Identify the shortest cycle for each cluster c in terms of hops by calculating the length l of the cycle w of the cluster c: $w_{l_c}$. If a shortest cycle exists, the first run of the breadth of the first search until achieving c will achieve the shortest cycle for the cluster. A generative potential $g_s$ may be generated for each scaffold:

$$g_s = \sum_i^{C_s} \left( \frac{\text{mean } (|C_s|)}{|C_i|} \right) \times w_{l_C}$$

Generative potential $g_s$ is normalized between 0 and 1. A high generative potential $g_s$ indicates the scaffold appears in small clusters with large cycle length. In other words, a high generative potential $g_s$ indicates a scaffold is part of bigger loops and flares in the topographical analysis graph and thus have a high likelihood of generating new molecules when subjected to scaffold-based generation.

A VAE loss function may be modified to include the generative potential $g_s$ of a molecular scaffold. A standard VAE loss function may be expressed as:

$$L=L_r+L_{KL}$$

Loss l for a single data point (G; S) for molecular graph G and corresponding scaffold S may be expressed as:

$$l_i(\Phi, \theta)=- \mathbb{E}_{z \sim q\Phi}[\log_{p_\theta}(G; S|z)]+KL[q_\Phi(z|G; S)\|p(z)]$$

The scaffold generative potential $g_s$ may be integrated into the loss function l to obtain:

$$l_i(\Phi, \theta)=g_s(- \mathbb{E}_{z \sim q\Phi}[\log_{p_\theta}(G; S|z)]+KL[q_\Phi(z|G; S)\|p(z)]+\alpha(g_{sn}-g_{sn}))$$

wherein $g_s$ is the generative potential of the input scaffold, $g_{sn}$ is the generative potential of the scaffold of a newly generated molecule $\hat{G}$ in the graph $G=(C, E)$, and $\alpha$ is a hyperparameter [0, 1].

The standard VAE loss function may thus be modified loss function:

$$L=(l-g_s)(L_r+L_{KM}+a(g_s-g_{sn}))$$

wherein $g_s$ is the generative potential of the input scaffold, $g_{sn}$ is the generative potential of the scaffold of a newly generated molecule $\hat{G}$ in the graph $G=(C, E)$, $\alpha$ is a hyperparameter [0, 1], $L_r$ is the reconstruction error of the inputs and generated scaffold $s_n$, and $L_{KL}$ is the Kullback-Leibler divergence between the prior and approximate posterior distribution.

Using a modified loss function enables the reduction of the influence of scaffolds which have low generative potential $g_s$ by penalizing models when the models generate molecules with low generative potential. To calculate the generative potential of scaffolds of newly generated molecules $g_{sn}$, newly generated molecules may be included in the graph after each iteration.

The most promising scaffolds in a dataset may be identified with the use of a modified loss function. Scaffolds in small clusters along big loops on the graph (e.g., Mapper graph) may be prioritized as such scaffolds may have the greatest generative potential $g_s$. Using the graph, the smallest loop in terms of hops may be identified in a variety of ways such as, for example, using any variant of the Dijkstra algorithm. The sum of the length of each edge in the loop, which is equivalent to the length of the cycle $w_l$, may be calculated. A large cycle length indicates a scaffold is part of a larger loop; thus, the likelihood of one or more desirable candidates increases. The Bemis-Murko scaffolds $S=\{s_1, s_2, \ldots s_n\}$ may be calculated for each molecule in the cluster. For each scaffold s, the generative potential $g_s$ may be calculated. Generative potential $g_s$ may be normalized between 0 and 1. A high generative potential $g_s$ indicates a scaffold appears in small clusters with large cycle length and, thus, has a high potential for generating new molecules.

Generating new molecules to complete loops in graphical data may employ graph-generative models for scaffold-based molecular design which have been adapted for the purpose of completing loops in graphical data. In some embodiments, VAEs may be used in the generative modeling process.

An input may be extended by sequentially adding atoms and bonds; in this way, molecular generation is conditioned on an input scaffold to ensure that all generated molecules contain the input scaffold. The VAE loss function may be modified to take into consideration the generative potential $g_s$ of the scaffolds.

Figure 6:
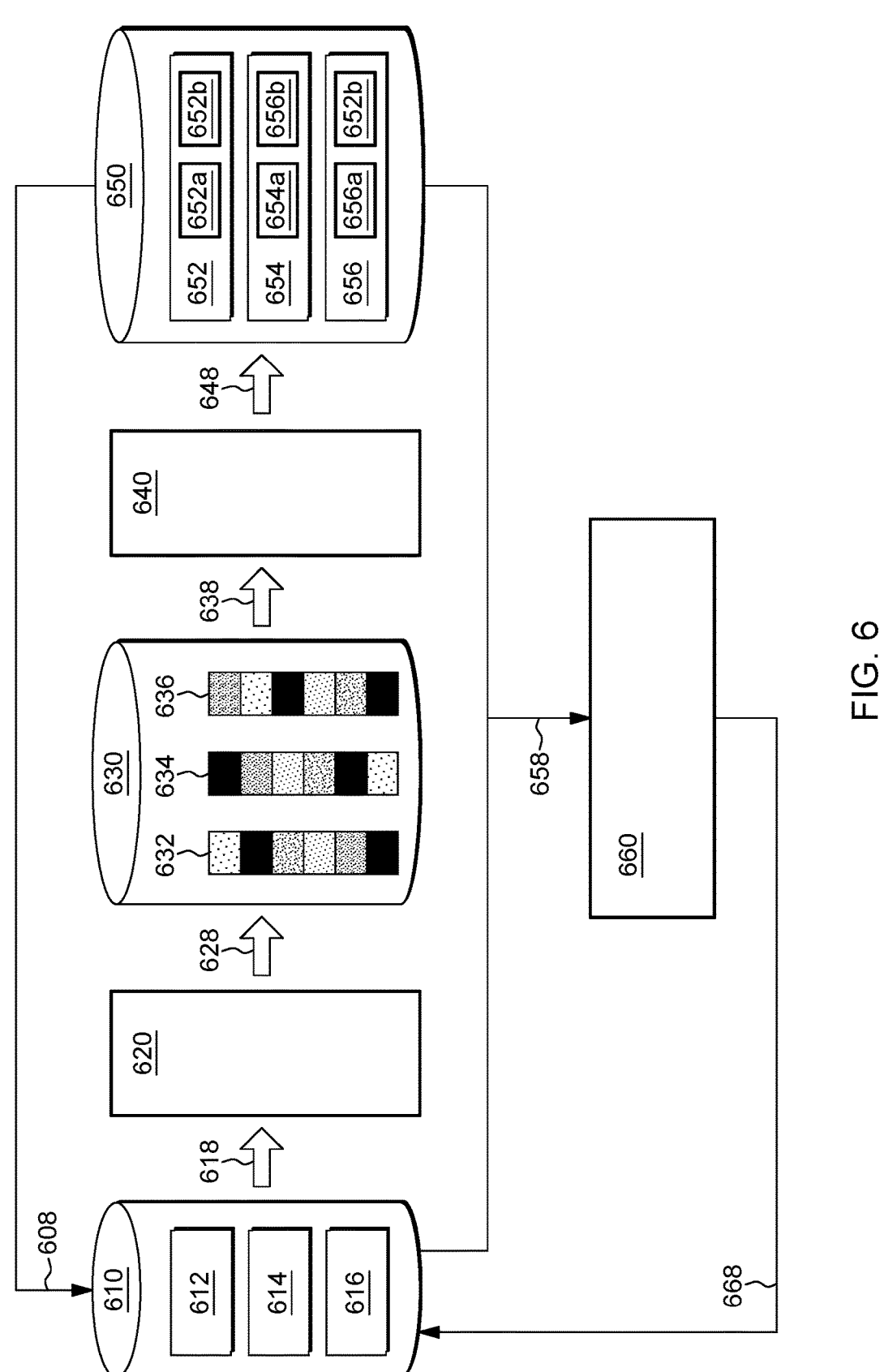
FIG. 6 illustrates a molecule generation pipeline in accordance with embodiments of the present disclosure.

FIG. 6 illustrates a molecule generation pipeline 600 in accordance with embodiments of the present disclosure. A molecular database 610 may contain data/information 612, 614, and 616 for molecules, molecular fragments, or some combination thereof. The molecular database 610 may originally contain reference molecular information that have been used and/or synthesized. The molecular database 610 may start with molecule information, molecular fragment information, or some combination thereof. The molecular database 610 may include information about synthesized molecules, synthesized molecular fragments, natural molecules, molecular fragments, or some combination thereof.

Molecular fragments may be fragmented according to empirical rules, randomly, or as decided by a user (e.g., a SME). Fragments may be combined in accordance with constraints manually selected and set by a user such as the number of fragments to combine, fragment compatibility, and fragment connectivity, among other constraints. A user may use algorithmic constraints for fragment combinations; for example, metaheuristics such as particle swarm optimization and genetic algorithm optimization may be used. In some embodiments of the present disclosure, a convolutional neural network (CNN) may be used to replicate SME decisions based on a set confidence threshold.

Information for a main molecular database 610 may be provided by literature (e.g., textbooks and chemical tables), subject matter experts, alternative sources, or some combination thereof. In some embodiments, the present disclosure provides for a system which analyzes new molecules it produces to complement an original molecular database 610 or establish a different molecular database 610 consisting of molecular data of newly generated molecules.

The molecular data 612, 614, and 616 may be submitted 618 to an encoder 620 to generate 628 molecular fingerprint data 632, 634, and 636 for a molecular fingerprint database 630. The molecular fingerprint database 630 may contain one or more molecular fingerprints 632, 634, and 636. Molecular fingerprints 632, 634, and 636 may be submitted 638 to a scaffold-conditioned VAE generator 640 to produce a candidate database 650 of molecular candidates 652a, 652b, 654a, 654b, 656a, and 656b from molecular scaffolds 652, 654, and 656.

Data for molecular scaffolds 652, 654, and 656 as well as new molecules 652a, 652b, 654a, 654b, 656a, and 656b may be contained in a candidate dataset 650 which may also be referred to as a dataset of newly generated molecules 650. The new molecules 652a, 652b, 654a, 654b, 656a, and 656b may be derived from the molecular scaffolds 652, 654, and 656. The molecular data concerning scaffolds 652, 654, and 656 and new molecules 652a, 652b, 654a, 654b, 656a, and 656b may be directly submitted 608 to the main molecular database 610 or may be submitted 658 to an analyzer 660 for analysis.

Molecular datasets 610 and 650 may be contributed 658 to an analyzer 660. In some embodiments, the analyzer 660 may gather information about the data that is to be submitted to the molecular dataset 610. In some embodiments, the analyzer 660 may be a system with predetermined analytical thresholds. In some embodiments, the analyzer 660 may be a SME. The analyzer 660 may analyze the molecular datasets 610 and 650 and submit 668 the results of the analyses to the main molecular dataset 610 to contribute to the molecule generation pipeline 600.

Figure 7:
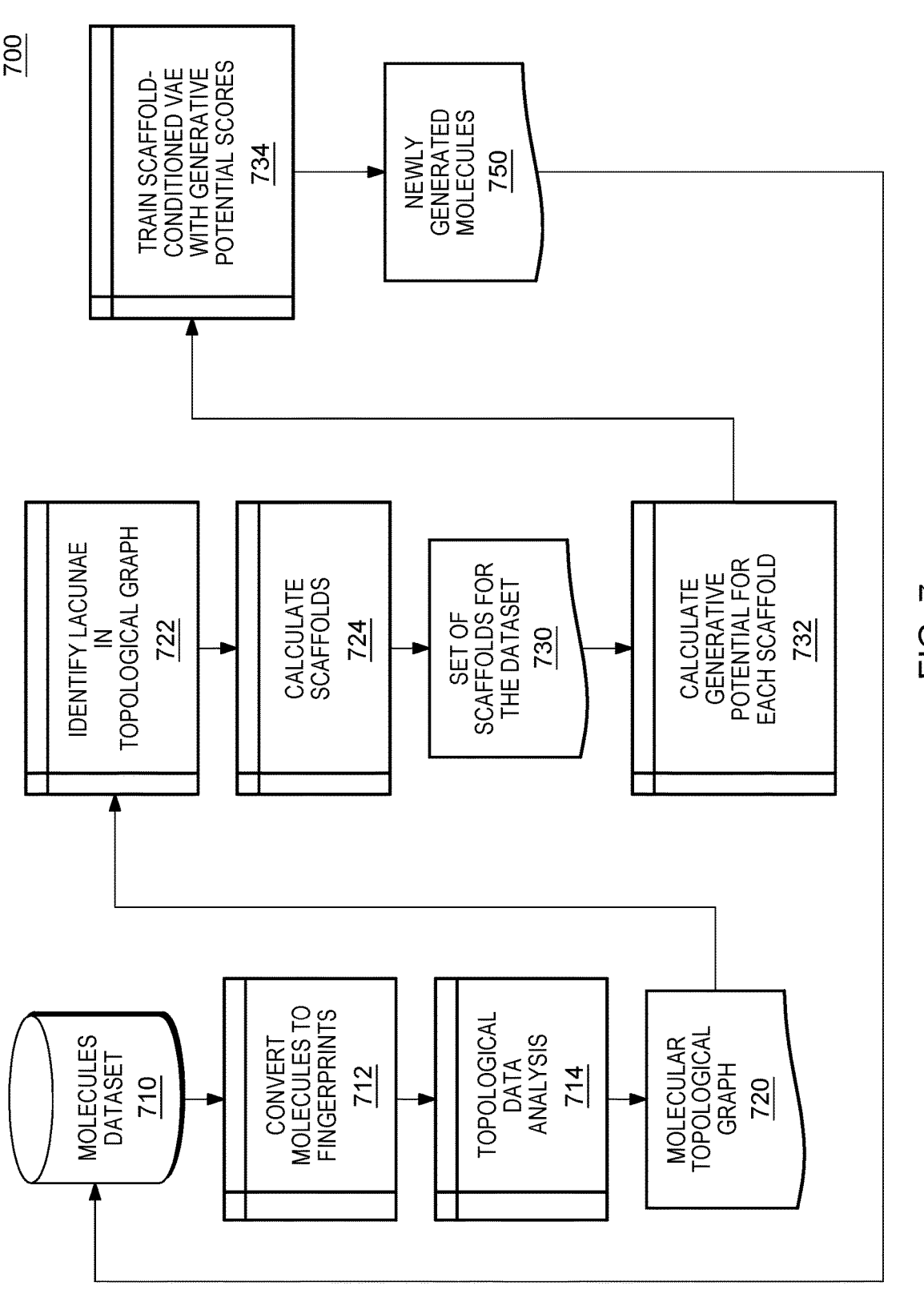
FIG. 7 illustrates a molecule generation pipeline in accordance with embodiments of the present disclosure.

FIG. 7 illustrates a molecule generation pipeline 700 in accordance with embodiments of the present disclosure. The cylinder 710 represents a corpus, the paned rectangles 712, 714, 722, 724, 732, and 734 represent a process, method, or function, and the wavy-bottomed rectangles 720, 730, and 750 represent an object or result.

With a molecular dataset 710, a molecule generation pipeline 700 may generate a topological graph 720 and scaffolds 730 for the dataset 710 to generate new molecules 750. Data about the new molecules 750 may be incorporated into the molecular dataset 710. Adding each new set of data from each round of new molecules 750 to the molecular dataset 710 enables cycling through the system 700 until potentially all lacunae are identified 722 and filled such that a particular molecular dataset 710 is completed to a point where no additional viable candidates are likely to be generated from the dataset.

In some embodiments of the present disclosure, generation of new molecules may be commenced with submitting one or more molecular datasets 710 to a molecular generation system 700. The system 700 may convert the molecules into molecular fingerprints 712 and perform a topological data analysis 714 on the molecular fingerprints. The topological data analysis 714 may produce a molecular topological graph 720.

The molecular topological graph 720 may be analyzed to identify lacunae in the topological graph 722. Identifying lacunae 722 may enable the calculating scaffolds 724 to fill the lacunae. Calculating scaffolds 724 for the identified lacunae 722 results in a set of scaffolds 730 for the molecular dataset 710.

The dataset scaffolds 730 may be used to calculate a generative potential score 732 for each of the scaffolds in the set of scaffolds 730. A scaffold-conditioned VAE may be trained 734 with the generative potential scores 732. The scaffold-conditioned VAE trained 734 with generative potential scores 732 may be used to generate one or more new molecules 750. New molecules 750 may be added to the molecular dataset 710. The process may be repeated until all lacunae in the molecular topological graph 720 are identified 722 and generation of new molecules 750 is complete for the dataset.

Some embodiments of the present disclosure may utilize cloud computing; thus, aspects of the disclosure may relate to cloud computing. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but the consumer has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software which may include operating systems and applications. The consumer does not manage or control the underlying cloud infrastructure but has control over operating systems, storage, and deployed applications, and the consumer possibly has limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and/or compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
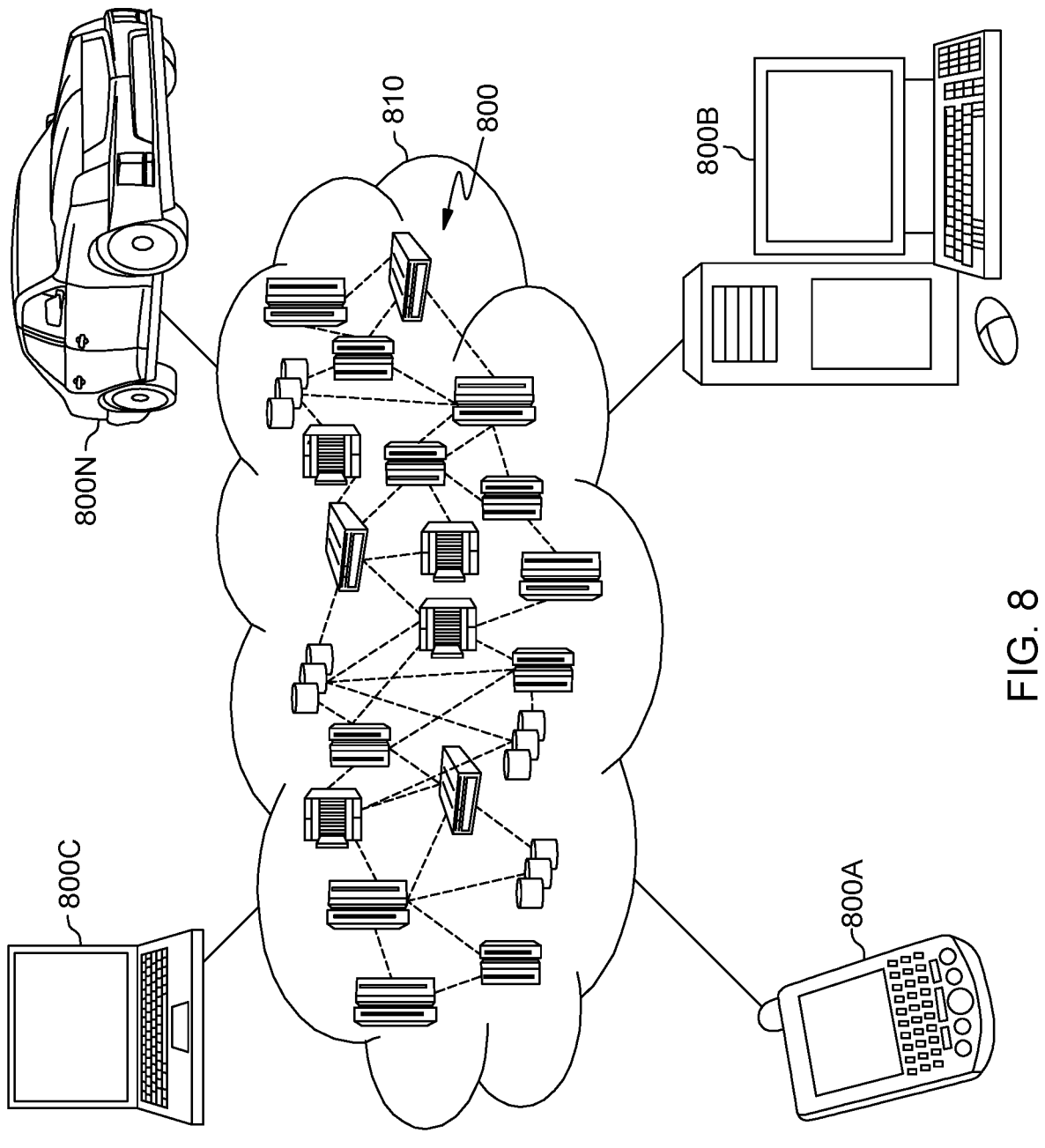
FIG. 8 illustrates a cloud computing environment, in accordance with embodiments of the present disclosure.

FIG. 8 illustrates a cloud computing environment 810 in accordance with embodiments of the present disclosure. As shown, cloud computing environment 810 includes one or more cloud computing nodes 800 with which local computing devices used by cloud consumers such as, for example, personal digital assistant (PDA) or cellular telephone 800A, desktop computer 800B, laptop computer 800C, and/or automobile computer system 800N may communicate. Nodes 800 may communicate with one another. They may be grouped (not shown) physically or virtually, in one or more networks, such as private, community, public, or hybrid clouds as described hereinabove, or a combination thereof.

This allows cloud computing environment 810 to offer infrastructure, platforms, and/or software as services for which a cloud consumer does not need to maintain resources on a local computing device. It is understood that the types of computing devices 800A-N shown in FIG. 8 are intended to be illustrative only and that computing nodes 800 and cloud computing environment 810 can communicate with any type of computerized device over any type of network and/or network addressable connection (e.g., using a web browser).

Figure 9:
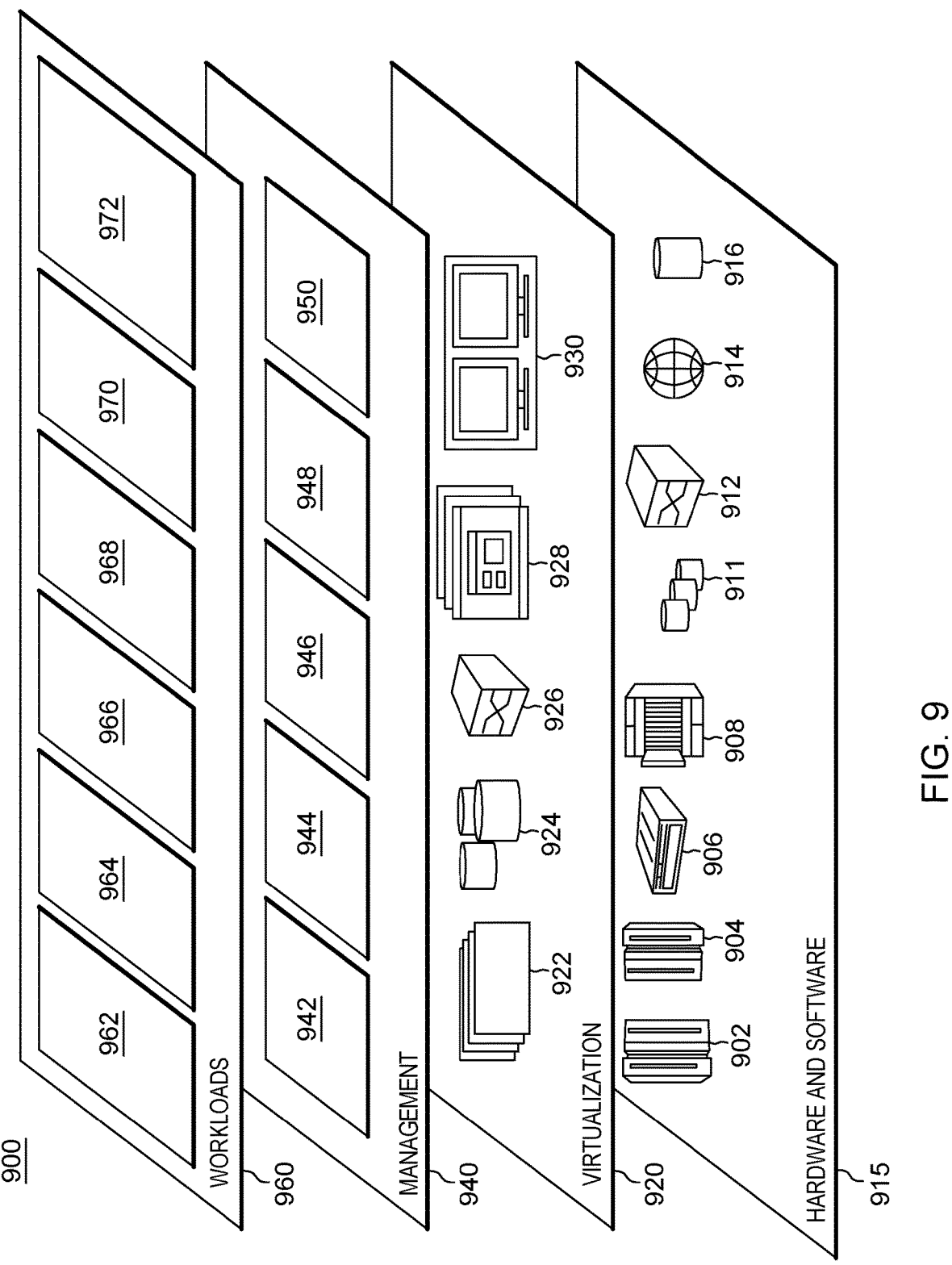
FIG. 9 depicts abstraction model layers, in accordance with embodiments of the present disclosure.

FIG. 9 illustrates abstraction model layers 900 provided by cloud computing environment 810 (FIG. 8) in accordance with embodiments of the present disclosure. It should be understood in advance that the components, layers, and functions shown in FIG. 9 are intended to be illustrative only and embodiments of the disclosure are not limited thereto. As depicted below, the following layers and corresponding functions are provided.

Hardware and software layer 915 includes hardware and software components. Examples of hardware components include: mainframes 902; RISC (Reduced Instruction Set Computer) architecture-based servers 904; servers 906; blade servers 908; storage devices 911; and networks and networking components 912. In some embodiments, software components include network application server software 914 and database software 916.

Virtualization layer 920 provides an abstraction layer from which the following examples of virtual entities may be provided: virtual servers 922; virtual storage 924; virtual networks 926, including virtual private networks; virtual applications and operating systems 928; and virtual clients 930.

In one example, management layer 940 may provide the functions described below. Resource provisioning 942 provides dynamic procurement of computing resources and other resources that are utilized to perform tasks within the cloud computing environment. Metering and pricing 944 provide cost tracking as resources and are utilized within the cloud computing environment as well as billing or invoicing for consumption of these resources. In one example, these resources may include application software licenses. Security provides identity verification for cloud consumers and tasks as well as protection for data and other resources. User portal 946 provides access to the cloud computing environment for consumers and system administrators. Service level management 948 provides cloud computing resource allocation and management such that required service levels are met. Service level agreement (SLA) planning and fulfillment 950 provide pre-arrangement for, and procurement of, cloud computing resources for which a future requirement is anticipated in accordance with an SLA.

Workloads layer 960 provides examples of functionality for which the cloud computing environment may be utilized. Examples of workloads and functions which may be provided from this layer include: mapping and navigation 962; software development and lifecycle management 964; virtual classroom education delivery 966; data analytics processing 968; transaction processing 970; and a tool for generating new molecules 972.

Figure 10:
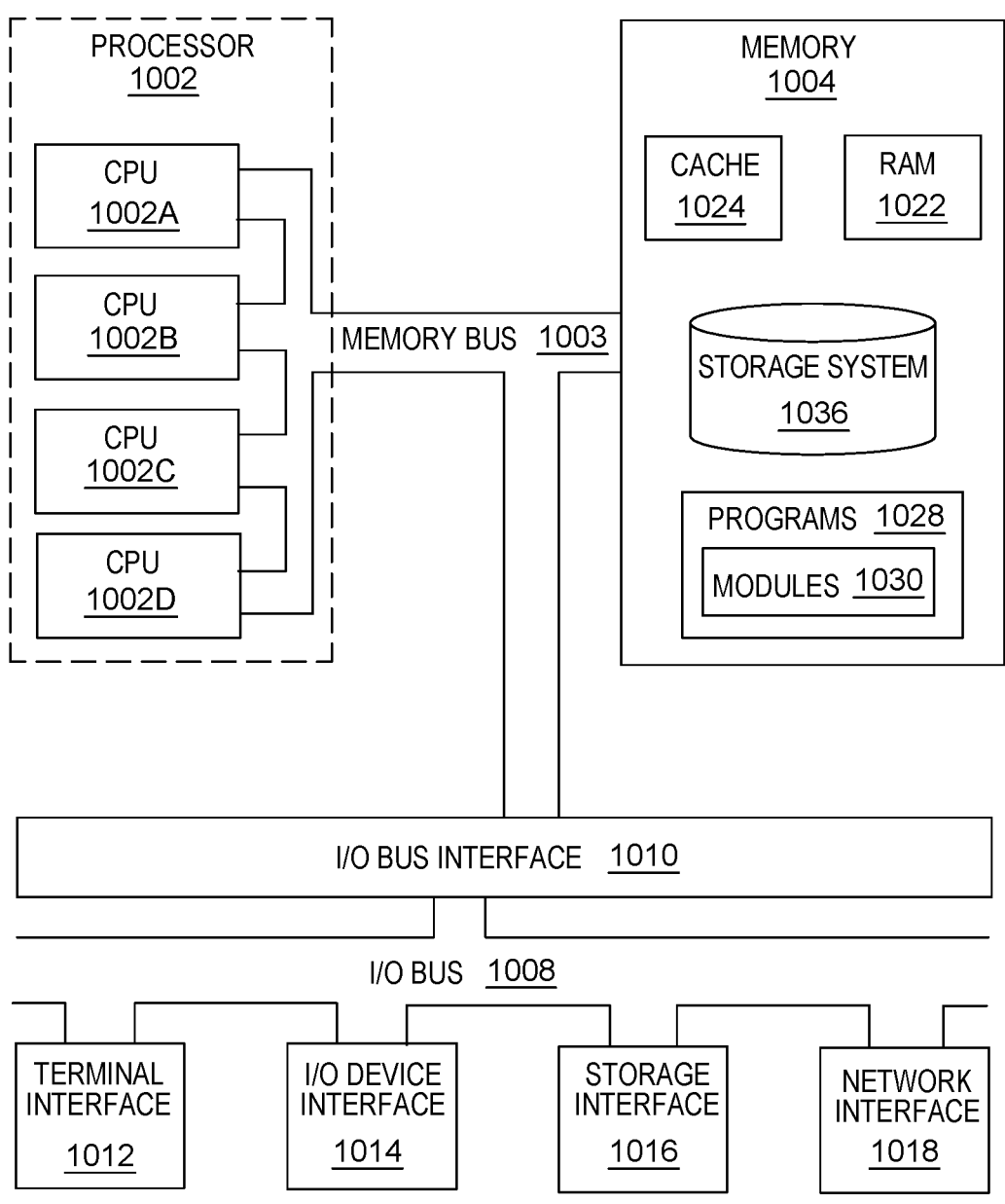
FIG. 10 illustrates a high-level block diagram of an example computer system that may be used in implementing one or more of the methods, tools, and modules, and any related functions, described herein, in accordance with embodiments of the present disclosure.

FIG. 10 illustrates a high-level block diagram of an example computer system 1001 that may be used in implementing one or more of the methods, tools, and modules, and any related functions, described herein (e.g., using one or more processor circuits or computer processors of the computer) in accordance with embodiments of the present disclosure. In some embodiments, the major components of the computer system 1001 may comprise a processor 1002 with one or more central processing units (CPUs) 1002A, 1002B, 1002C, and 1002D, a memory subsystem 1004, a terminal interface 1012, a storage interface 1016, an I/O (Input/Output) device interface 1014, and a network interface 1018, all of which may be communicatively coupled, directly or indirectly, for inter-component communication via a memory bus 1003, an I/O bus 1008, and an I/O bus interface unit 1010.

The computer system 1001 may contain one or more general-purpose programmable CPUs 1002A, 1002B, 1002C, and 1002D, herein generically referred to as the CPU 1002. In some embodiments, the computer system 1001 may contain multiple processors typical of a relatively large system; however, in other embodiments, the computer system 1001 may alternatively be a single CPU system. Each CPU 1002 may execute instructions stored in the memory subsystem 1004 and may include one or more levels of on-board cache.

System memory 1004 may include computer system readable media in the form of volatile memory, such as random access memory (RAM) 1022 or cache memory 1024. Computer system 1001 may further include other removable/non-removable, volatile/non-volatile computer system storage media. By way of example only, storage system 1026 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM, or other optical media can be provided. In addition, memory 1004 can include flash memory, e.g., a flash memory stick drive or a flash drive. Memory devices can be connected to memory bus 1003 by one or more data media interfaces. The memory 1004 may include at least one program product having a set (e.g., at least one) of program modules that are configured to carry out the functions of various embodiments.

One or more programs/utilities 1028, each having at least one set of program modules 830, may be stored in memory 1004. The programs/utilities 1028 may include a hypervisor (also referred to as a virtual machine monitor), one or more operating systems, one or more application programs, other program modules, and program data. Each of the operating systems, one or more application programs, other program modules, and program data, or some combination thereof, may include an implementation of a networking environment. Programs 1028 and/or program modules 1030 generally perform the functions or methodologies of various embodiments.

Although the memory bus 1003 is shown in FIG. 10 as a single bus structure providing a direct communication path among the CPUs 1002, the memory subsystem 1004, and the I/O bus interface 1010, the memory bus 1003 may, in some embodiments, include multiple different buses or communication paths, which may be arranged in any of various forms, such as point-to-point links in hierarchical, star, or web configurations, multiple hierarchical buses, parallel and redundant paths, or any other appropriate type of configuration. Furthermore, while the I/O bus interface 1010 and the I/O bus 1008 are shown as single respective units, the computer system 1001 may, in some embodiments, contain multiple I/O bus interface units 1010, multiple I/O buses 1008, or both. Further, while multiple I/O interface units 1010 are shown, which separate the I/O bus 1008 from various communications paths running to the various I/O devices, in other embodiments some or all of the I/O devices may be connected directly to one or more system I/O buses 1008.

In some embodiments, the computer system 1001 may be a multi-user mainframe computer system, a single-user system, a server computer, or similar device that has little or no direct user interface but receives requests from other computer systems (clients). Further, in some embodiments, the computer system 1001 may be implemented as a desktop computer, portable computer, laptop or notebook computer, tablet computer, pocket computer, telephone, smartphone, network switches or routers, or any other appropriate type of electronic device.

It is noted that FIG. 10 is intended to depict the representative major components of an exemplary computer system 1001. In some embodiments, however, individual components may have greater or lesser complexity than as represented in FIG. 10, components other than or in addition to those shown in FIG. 10 may be present, and the number, type, and configuration of such components may vary.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment currently known or that which may be later developed.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide, or other transmission media (e.g., light pulses passing through a fiber-optic cable) or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer, or entirely on a remote computer or server. In the latter scenario, the remote computer may be connected to the user's computer through any type of network, including a local area network (LAN) or a wide area network (WAN) or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The present disclosure discusses a method, system, and computer program product for generating new molecules. The present disclosure discusses receiving molecular data for a plurality of molecules, performing a topological data analysis on the molecular data to generate a molecular topological map, identifying one or more lacunae in the molecular topological map, and generating one or more additional molecules to fill at least one of the one or more lacunae.

The present disclosure further discusses the plurality of molecules have one or more molecular properties in common. The present disclosure further discusses generating a molecular scaffold for each of the plurality of molecules. The present disclosure further discusses generating a generative potential score for each scaffold. The present disclosure further discusses the plurality of molecules sharing a molecular scaffold, and wherein the one or more additional molecules contain the molecular scaffold.

The present disclosure further discusses the one or more additional molecules are generated using a variational autoencoder. The present disclosure further discusses conditioning the variational autoencoder via scaffold-conditioning such that the one or more additional molecules contain a specified molecular scaffold. The present disclosure further discusses the variational autoencoder has a variational autoencoder loss function and modifying the variational autoencoder loss function to include a generative potential of the specified molecular scaffold.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions which comprises one or more executable instructions for implementing the specified logical function(s). In some alternative implementations, the functions noted in the blocks may occur out of the order noted in the figures. For example, two blocks shown in succession may, in fact, be accomplished as one step, executed concurrently, substantially concurrently, in a partially or wholly temporally overlapping manner, or the blocks may sometimes be executed in the reverse order depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or the technical improvement over technologies found in the marketplace or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

The invention claimed is:

1. A method for generating new molecules, said method comprising:

receiving molecular data for a plurality of molecules, wherein said molecular data includes molecular features;

determining a molecular fingerprint for each of said plurality of molecules with an encoder based on said molecular data;

performing a topological data analysis on said molecular data with said encoder to generate a molecular topological graph, wherein said molecular data includes said molecular fingerprint for each of said plurality of molecules;

calculating a generative potential score for said plurality of molecules;

training a scaffold-conditioned variational autoencoder with said generative potential scores, wherein said scaffold-conditioned variational autoencoder is conditioned on an input scaffold;

identifying one or more lacunae in said molecular topological graph; and generating, using said scaffold-conditioned variational autoencoder, one or more additional molecules to fill at least one of said one or more lacunae, wherein said one or more additional molecules each contain said input scaffold.

2. The method of claim 1 wherein said plurality of molecules have one or more molecular properties in common.

3. The method of claim 1 further comprising:
generating a molecular scaffold for each of said plurality of molecules.

4. The method of claim 3 further comprising:
generating a scaffold generative potential score for each scaffold.

5. The method of claim 1 wherein said plurality of molecules share a molecular scaffold, and wherein said one or more additional molecules contain said molecular scaffold.

6. The method of claim 1 wherein said scaffold-conditioned variational autoencoder has a variational autoencoder loss function, and wherein said method further comprises:
modifying said variational autoencoder loss function to include a generative potential of a specified molecular scaffold.

7. The method of claim 1 wherein said identifying said one or more lacunae comprises:
analyzing said molecular topological graph with said encoder.

8. The method of claim 1 further comprising:
generating a scaffold for each of said one or more lacunae with said encoder.

9. The method of claim 1 wherein:
each of said one or more additional molecules change a topology of said molecular topological graph.

10. The method of claim 1 wherein each of said one or more additional molecules has additional molecule molecular data, further comprising:
incorporating said additional molecule molecular data into said molecular data; and
updating said topological data analysis to include said additional molecule molecular data.

11. The method of claim 1, further comprising:
conditioning said scaffold-conditioned variational autoencoder with said input scaffold.

12. A system that generates new molecules, said system comprising:
a memory; and
a processor in communication with said memory, said processor being configured to perform operations comprising:
receiving molecular data for a plurality of molecules, wherein said molecular data includes molecular features;
determining a molecular fingerprint for each of said plurality of molecules with an encoder based on said molecular data;
performing a topological data analysis on said molecular data with said encoder to generate a molecular topological graph, wherein said molecular data includes said molecular fingerprint for each of said plurality of molecules;
calculating a generative potential score for said plurality of molecules;
training a scaffold-conditioned variational autoencoder with said generative potential scores, wherein said scaffold-conditioned variational autoencoder is conditioned on an input scaffold;
identifying one or more lacunae in said molecular topological graph; and generating, using said scaffold-conditioned variational autoencoder, one or more additional molecules to fill at least one of said one or more lacunae, wherein said one or more additional molecules each contain said input scaffold.

13. The system of claim 12 further comprising:
generating a molecular scaffold for each of said plurality of molecules.

14. The system of claim 13 further comprising:
generating a scaffold generative potential score for each scaffold.

15. The system of claim 12 wherein said plurality of molecules share a molecular scaffold, and wherein said one or more additional molecules contain said molecular scaffold.

16. The system of claim 12 wherein said scaffold-conditioned variational autoencoder has a variational autoencoder loss function, and wherein said operations further comprise:
modifying said variational autoencoder loss function to include a generative potential of a specified molecular scaffold.

17. A computer program product for generating new molecules, said computer program product comprising a computer readable storage medium having program instructions embodied therewith, said program instructions executable by a processor to cause said processor perform a function, said function comprising:
receiving molecular data for a plurality of molecules, wherein said molecular data includes molecular features;
determining a molecular fingerprint for each of said plurality of molecules with an encoder based on said molecular data;
performing a topological data analysis on said molecular data with said encoder to generate a molecular topological graph, wherein said molecular data includes said molecular fingerprint for each of said plurality of molecules;
calculating a generative potential score for said plurality of molecules;
training a scaffold-conditioned variational autoencoder with said generative potential scores, wherein said scaffold-conditioned variational autoencoder is conditioned on an input scaffold;
identifying one or more lacunae in said molecular topological graph; and
generating, using said scaffold-conditioned variational autoencoder, one or more additional molecules to fill at least one of said one or more lacunae, wherein said one or more additional molecules each contain said input scaffold.

18. The computer program product of claim 17 further comprising:
generating a molecular scaffold for each of said plurality of molecules; and
generating a scaffold generative potential score for each scaffold.

19. The computer program product of claim 17 wherein:
said scaffold-conditioned variational autoencoder is conditioned such that said one or more additional molecules contain a specified molecular scaffold.

20. The computer program product of claim 19 wherein said scaffold-conditioned variational autoencoder has a variational autoencoder loss function, and wherein said function further comprises:

modifying said variational autoencoder loss function to include a generative potential of a specified molecular scaffold.

* * * * *